(12) United States Patent
Feng et al.

(10) Patent No.: US 6,752,754 B1
(45) Date of Patent: Jun. 22, 2004

(54) ARTIFICIAL RECTUM AND RELATED METHOD

(75) Inventors: Weimin Feng, Wakefield, MA (US); Steven Z. Yang, Guilford, CT (US)

(73) Assignee: Imagine Enterprise, Inc., Wakefield, MA (US)

( * ) Notice: Subject to any disclaimer, the term of this patent is extended or adjusted under 35 U.S.C. 154(b) by 0 days.

(21) Appl. No.: 10/357,697

(22) Filed: Feb. 4, 2003

(51) Int. Cl.[7] ............................... A61F 2/02; A61F 2/08
(52) U.S. Cl. ...................................... 600/30; 623/14.13
(58) Field of Search ............................... 600/30, 29, 31, 600/32; 128/899, DIG. 25; 623/14.13; 604/175, 328, 332, 103.03, 339, 907, 34, 277, 335; 606/197, 198, 192; 525/53, 313, 316; 251/7, 9; 280/124.116, 124.163, 124.174; 267/31

(56) References Cited

U.S. PATENT DOCUMENTS

| | | | | |
|---|---|---|---|---|
| 3,802,718 A | * | 4/1974 | Schaeff ................ 280/124.116 |
| 3,828,782 A | * | 8/1974 | Polin ...................... 604/103.03 |
| 4,204,282 A | * | 5/1980 | Bolt ......................... 623/14.13 |
| 4,217,899 A | | 8/1980 | Freir ............................ 128/283 |
| 4,351,322 A | * | 9/1982 | Prager ........................... 600/32 |
| 4,401,107 A | * | 8/1983 | Haber et al. .................. 600/30 |
| 4,596,554 A | | 6/1986 | Dastgeer ....................... 604/54 |
| 4,634,421 A | * | 1/1987 | Hegemann .................... 604/34 |
| 4,682,583 A | * | 7/1987 | Burton et al. ................. 600/31 |
| 4,705,518 A | * | 11/1987 | Baker et al. .............. 623/14.13 |
| 4,904,256 A | * | 2/1990 | Yamaguchi .............. 623/14.13 |
| 4,986,822 A | | 1/1991 | Anderson ................... 604/276 |
| 4,994,019 A | | 2/1991 | Fernandez et al. ............ 600/30 |
| 5,000,750 A | | 3/1991 | Leveen et al. ................. 606/1 |
| 5,210,132 A | * | 5/1993 | Matsubara et al. ........... 525/53 |
| 5,380,268 A | * | 1/1995 | Wheeler ....................... 600/30 |
| 5,795,288 A | * | 8/1998 | Cohen et al. ................. 600/29 |
| 6,096,057 A | * | 8/2000 | Klingenstein ............... 606/197 |
| 6,491,623 B2 | * | 12/2002 | Snyder et al. ................ 600/31 |
| 2001/0023337 A1 | | 9/2001 | Lapcevic ..................... 604/332 |

FOREIGN PATENT DOCUMENTS

| | | |
|---|---|---|
| JP | 2000325483 | 11/2000 |
| JP | 2001046493 | 2/2001 |
| JP | 2001137333 | 5/2001 |
| JP | 2001170163 | 6/2001 |

* cited by examiner

*Primary Examiner*—Eric F. Winakur
*Assistant Examiner*—Nikita R Veniaminov
(74) *Attorney, Agent, or Firm*—McCarter & English, LLP

(57) ABSTRACT

An implantable device for selectively controlling defecation has an outer body defining on one end a flange that is surgically attachable to the patient's anus and/or tissue adjacent to the anus. A connector is mounted on the other end of the outer body and is secured to the distal end of the patient's large intestine for connecting the large intestine in fluid communication with the artificial rectum. An inner body is slidably received within the outer body. A macerator-type pump is mounted within the inner body and an inlet valve is mounted between the pump and the connector. An actuator in the form of an RF receiver is electrically coupled to the inlet valve and the pump and a remote transmitter is operatively coupled to the receiver. The receiver is responsive to control signals received from the transmitter to open the inlet valve and operate the pump in order to move fecal matter through the artificial rectum.

26 Claims, 5 Drawing Sheets

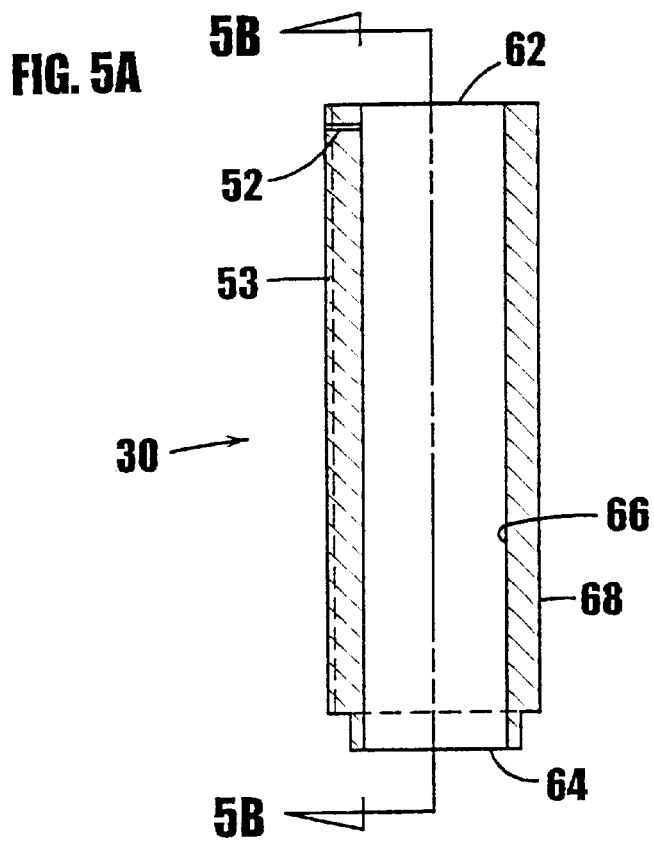
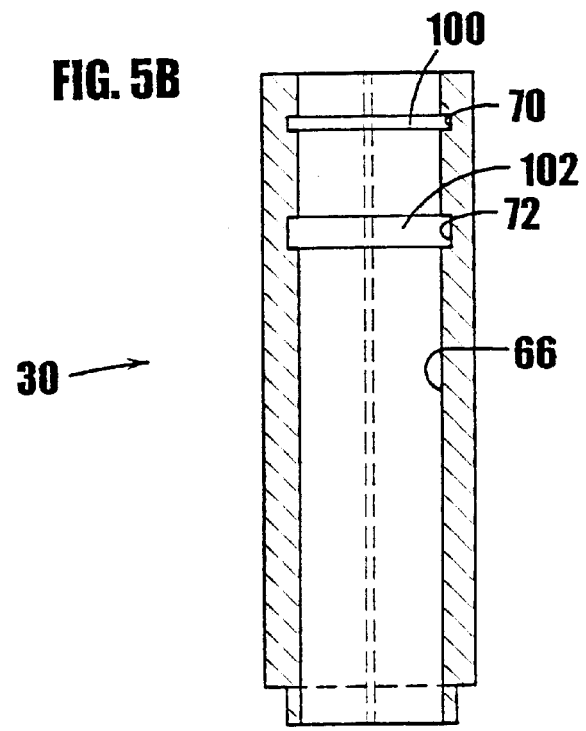

ARTIFICIAL RECTUM AND RELATED METHOD

BACKGROUND OF THE INVENTION

1. Field of the Invention

The present invention relates to the devices and methods for controlling the excretion of waste from the human body, and more particularly, to an artificial rectum and method for selectively controlling defecation in colostomy patients due to colorectal cancer, disease, injury, birth defect, or other causes.

2. Background of the Related Art

The rectum with sphincter musculature provides the collection point and discharge mechanism for waste elimination. Cancers of the colon and rectum are two of the most common cancers in the United States. Together, they are referred to as colorectal cancer.

Surgical removal of a malignant tumor is the most common treatment for colorectal cancer. The diseased portion of the colon and/or rectum is removed, and in most cases, the healthy portions are reattached. However, approximately 5% of patients with colorectal cancer require a colostomy because of the extent of the disease or its location. In such cases, a surgical opening is made through the abdomen to provide a new path for waste elimination, whereby the patient is required to excrete through a stoma (small aperture in the skin) and into a colostomy bag. Since the colostomy bag can only be used for liquid feces, the surgeon also removes the large intestine, even though a majority of it might be healthy, in order to prevent the formation of any solid feces and thereby ensure the proper passage of the feces through the stoma and into the colostomy bag.

A colostomy also may be performed to treat traumatic injuries to the bowel, diverticulitis, and inflammatory bowel disease, when other treatment measures fail. Currently, there is a population of about 850,000 people in North America that live with the condition, with about 7,000 new cases of colostomy due to colorectal cancer reported annually based on Cleveland Clinic statistics. Worldwide, U.N. statistics estimate 3.5 million patients in developed countries alone live with colostomy.

Several devices have been developed to allow such patients limited control over their need to eliminate wastes from their bodies. For example, U.S. Patent application Ser. No. 2001/00223337 A1 to Lapcevic shows an apparatus that evacuates human waste products from a stoma which includes a battery-powered or manual evacuator pump activated by an external switch or operator to empty the shortened bowel. The evacuator assembly is adapted to seal over the stoma during operation, after which it may be removed.

Further examples include U.S. Pat. No. 4,351,322 to Prager which shows a stoma control device having a ring for surgical implantation around an emerging bowel. A plug is adapted to fit within the distal end of the bowel which selectively inflates to engage the surrounding tissue and ring to block the stoma.

Still further, U.S. Pat. No. 4,217,899 to Freir shows a prosthesis permanently attached to the distal end of the intestinal tract that allows waste products to accumulate. Elimination of the waste products is through a removable assembly of an elastic liner and support structure that communicates with the affixed portion of the prosthesis to collect the waste.

In light of the foregoing, a need exists for an artificial rectum which provides selective control over the excretion of fecal matter to obviate the need for removal of the large intestine in a patient and the associated use of a stoma for collection/removal of waste products.

SUMMARY OF THE INVENTION

The present invention is directed to an artificial rectum and method for selectively moving feces through the lower gastro-intestinal tract and out of the body. Accordingly, a principal advantage of the present invention is the elimination of the need for a colostomy bag and stoma in patients who undergo a colostomy. An inlet to the artificial rectum is operatively connected to the distal end of the large intestine, and communicates fecal waste to a one-way liquid-tight inlet valve and pump, such as a macerator-type pump, mounted within an inner body substantially inserted into and retained by an outer body of the artificial rectum. The inlet valve and pump work in tandem to control the flow of fecal matter through the artificial rectum and out of the body. Such a configuration has the added advantage of permitting removal of the inner body from the permanently installed outer body of the artificial rectum for subsequent medical examination of the large intestine (e.g. coloscopy) or replacement of the inner body and moveable parts mounted thereto. An outlet or tissue ingrowth flange is formed on the external end of the outer body and can be surgically connected to the patient's skin surrounding the remaining portion of the sphincter muscle. In use, the patient actuates a remote control unit, for example, to open the inlet valve and drive an impeller of the pump to discharge feces therethrough. The patient ceases defecation by stopping the impeller and shutting the inlet valve.

In a currently preferred embodiment of the present invention, the artificial rectum includes means for permitting the patient to selectively control the operation of the artificial rectum. In one such embodiment, control is achieved through the use of a remote control unit functionally coupled, such as by RF, to the pump and/or inlet valve.

Another embodiment of the present invention includes a one-way liquid-tight valve extending through a side-wall of the artificial rectum and connected in fluid communication to an outlet conduit to allow the release of gaseous waste.

The present invention also is directed to a method for providing selective control of defecation by a colostomy patient. The method comprises the following steps:

providing an artificial rectum having an inlet, an outlet, and a flow control device coupled in fluid communication between the inlet and the outlet;

connecting the inlet or tissue ingrowth collar of the artificial rectum in fluid communication with a large intestine of the patient;

connecting the outlet or tissue ingrowth flange of the artificial rectum to the anus and/or tissue adjacent to the anus of the patient; and receiving fecal matter from the large intestine through the inlet of the artificial rectum, and controlling the flow control device to selectively move the fecal matter between the inlet and the outlet, and, in turn, discharge the fecal matter through the outlet to thereby control defecation of the patient.

These and other unique features of the artificial rectum and method disclosed herein will become more readily apparent from the following detailed description of currently preferred embodiments, the accompanying drawings and the appended claims.

BRIEF DESCRIPTION OF THE DRAWINGS

So that those having ordinary skill in the art to which the disclosed artificial rectum and method appertain will more readily understand how to make and use the same, reference may be had to the drawings wherein:

FIG. 5A is a cross-sectional view of the inner body with one-way valve of the artificial rectum of FIG. 2;

FIG. 5B is a cross-sectional view of the inner body taken along line 5B—5B of FIG. 5A;

DETAILED DESCRIPTION OF THE PREFERRED EMBODIMENTS

Figure 1:
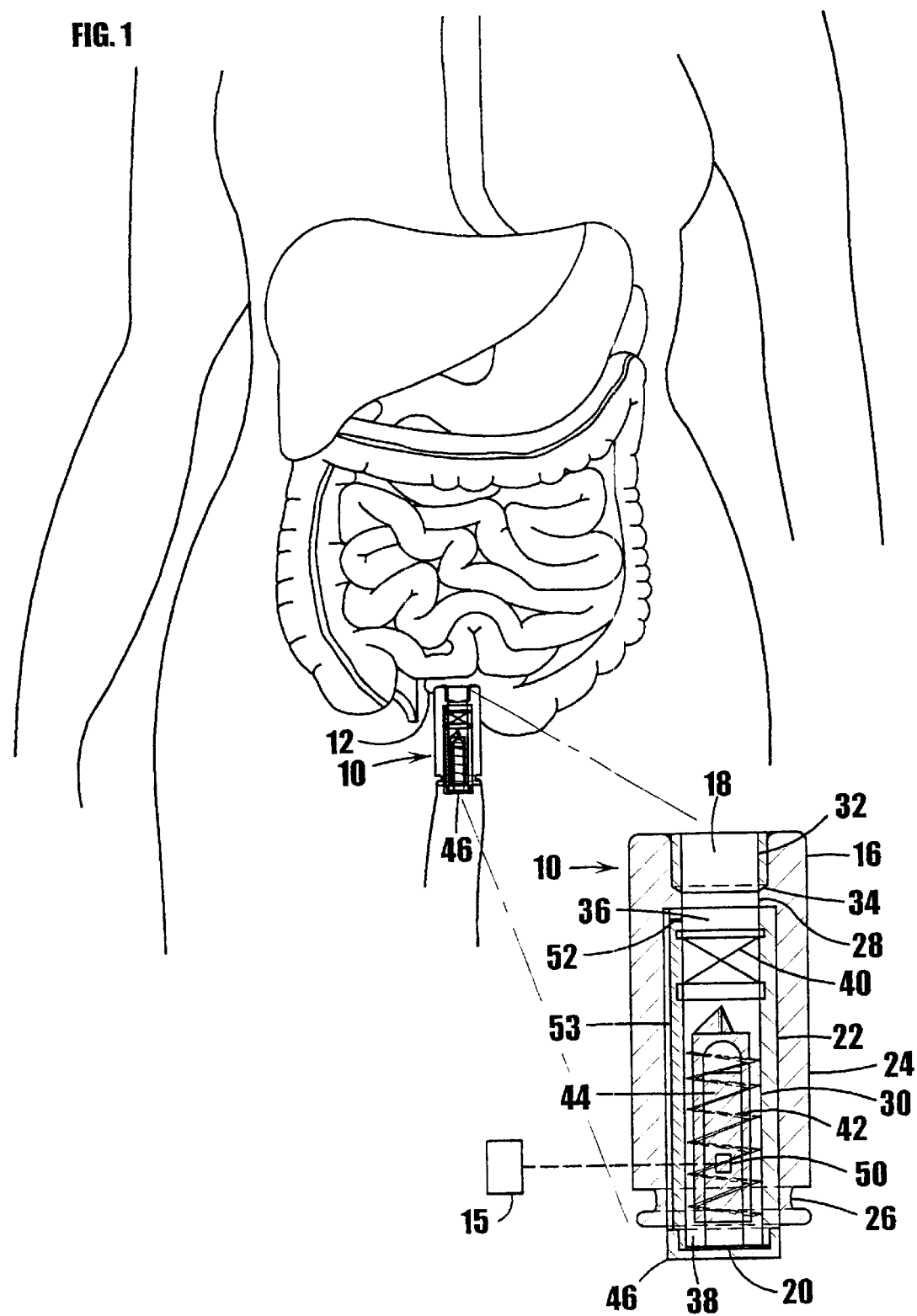
FIG. 1 illustrates an artificial rectum for selectively eliminating fecal matter from a patient, and in particular a sectional view of the lower abdominal and rectal region of a patient having the artificial rectum fully disposed in an operational position.

The subject disclosure relates to an improved device and method for controlling the discharge of feces from the body. The device and method are particularly applicable in an artificial rectum, although they may be utilized in many applications, such as to treat all manner of fecal incontinence, as would be readily appreciated by those skilled in the pertinent art. The advantages and other features of the device and method disclosed herein will become more readily apparent to those having ordinary skill in the pertinent art from the following detailed description of certain preferred embodiments of the invention taken in conjunction with the drawings which set forth representative embodiments of the present disclosure and wherein like reference numeral identify similar structures.

Referring to FIG. 1, there is shown an environment in which the representative embodiments of the artificial rectum may be used. As illustrated, an artificial rectum, designated generally by reference numeral 10, is substantially enclosed within the lower abdominal region of a patient and connected in fluid communication between the distal end of the patient's large intestine 12 and the anal sphincter muscle and adjacent tissue 14. The artificial rectum 10 is selectively actuated by the patient to control the flow of wastes from the large intestine through the use of an actuator 15. As described further below, the actuator 15 may take the form of any of numerous different actuators that are currently, or later become known for performing the function of the actuator described herein, such as a remote control unit, a switch mounted on the artificial rectum itself or adjacent thereto, or a sensor.

Figure 2:
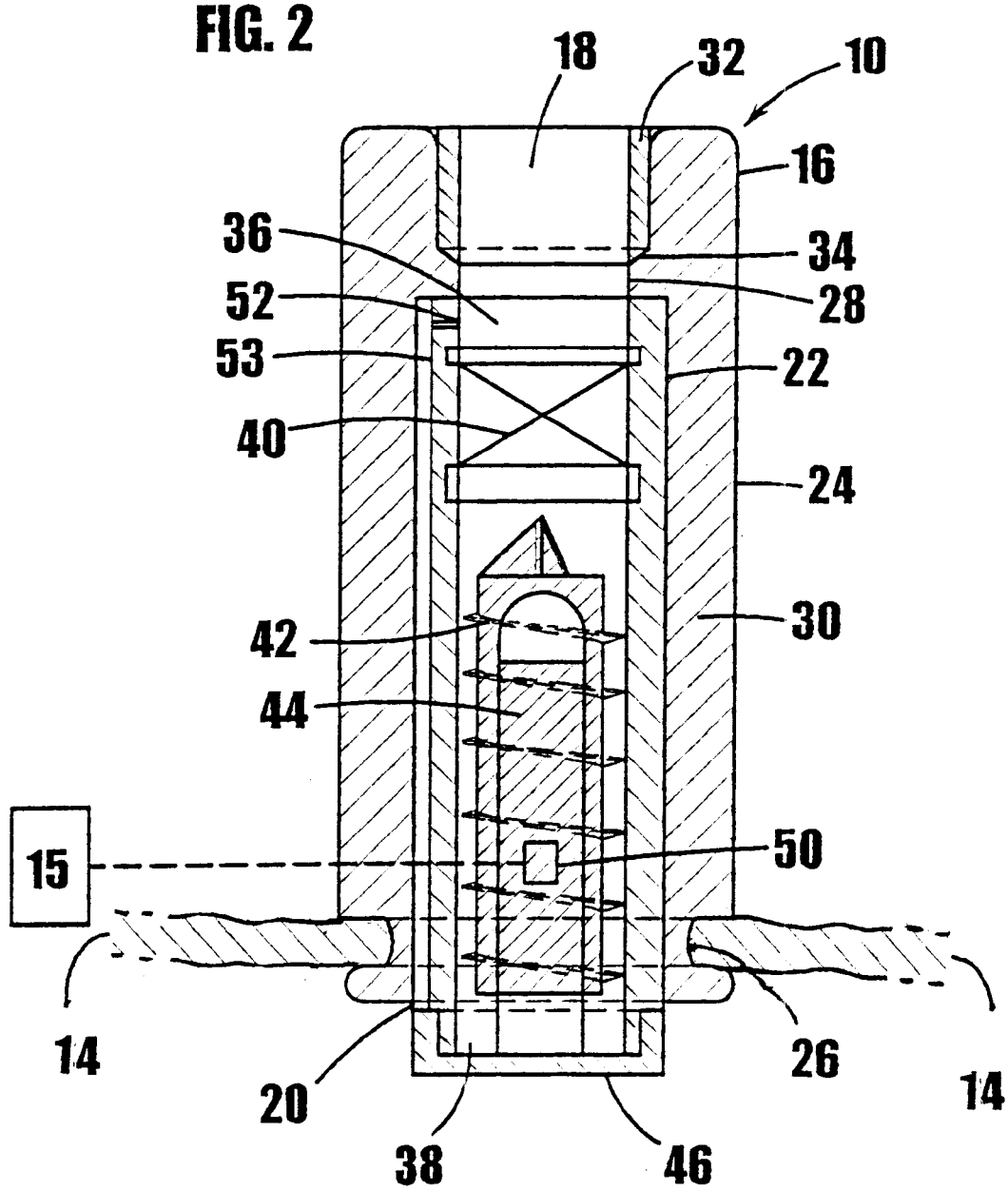
FIG. 2 is a cross-sectional view of an artificial rectum constructed in accordance with a preferred embodiment of the subject disclosure, wherein the artificial rectum includes an outer body, a connector, an inner body, an inlet valve, a pump, a motor, an RF receiver, a battery, and a cover.

Referring to FIG. 2, the artificial rectum 10 includes an outer body 16 defining an inlet in the form of a tissue ingrowth collar 18 and an outlet in the form of a tissue ingrowth flange 20 connected in fluid communication with the inlet. As shown typically in FIG. 1 and described further below, the outer body 16 is implanted into the colorectal cavity after removal of the rectum and anus. As shown in FIG. 2, the outer body 16 defines a first inner surface 22 and a first outer surface 24. The first outer surface 24 defines on one end an annular recess forming a mounting flange 26 at the outlet or tissue ingrowth flange 20 for surgical attachment, such as by surgical staples (not shown), to the patient's anal sphincter muscle or adjacent tissue 14. The first inner surface 22 defines in an upper portion thereof an inwardly-protruding annular shoulder 28. The annular shoulder 28 engages on one side thereof an inner body 30 inserted into the tissue ingrowth flange 20, and engages on another side thereof a connector 32 inserted into the inlet or tissue ingrowth collar 18 of the outer body and fixedly secured to the distal end of the large intestine 12, as described further below. In a currently preferred embodiment of the present invention, and as shown in FIG. 2, the inner seating surface of the annular shoulder 28 is substantially perpendicular to the first inner surface 22 for engaging the inner body 30, and the outer seating surface of the shoulder is beveled to receive a correspondingly beveled surface 34 of the connector 32 and distal portion of the large intestine 12 connected thereto, as described further below.

In the currently preferred embodiment of the artificial rectum, and as described further below, the connector 32 and distal portion of the large intestine 12 secured thereto form a press-fit seal with the inlet or tissue ingrowth collar 18 of the outer body 16. The inner body 30 defines a second inlet 36 on its inner end and a second outlet 38 on its outer end. An inlet valve 40 is mounted to the inner body 30 within or adjacent to the second inlet 36 and is opened to permit the flow of fecal matter therethrough. A macerator-type pump 42 is mounted within the inner body 30 downstream of the inlet valve 40, and is rotatably driven by a motor 44 powered by a battery 46 to induce movement of fecal matter from the inlet or tissue ingrowth collar 18, through the inlet valve 40 and pump 42 and, in turn, through the outlet or tissue ingrowth flange 20 and out of the body. Thus, the macerator-type pump 42 operates in tandem with the inlet valve 40 to selectively control the flow of fecal matter through the artificial rectum, and in turn, out of the patient's body. However, as may be recognized by those skilled in the pertinent art based on the teachings herein, the valve and/or pump may take any of numerous different configurations that are currently or later become known. In addition, the artificial rectum may include a pump without any valves, or one or more valves without a pump. An air-tight removable cover 48 is provided to occlude the second outlet 38 when the artificial rectum is not in operation to thereby prevent the fecal odor leaking from the artificial rectum.

As shown in FIGS. 1 and 2, the inlet valve 40 and macerator-type pump 42 are actuated by a remote receiver 50 that is functionally coupled, such as by RF, to the remote control unit 15 to allow the patient to control their operation. As indicated above, the actuator need not take the form of the receiver 50 and/or remote control unit 15, but rather may take the form of any of numerous different actuators that are currently or later become known for performing the function of the actuator as described herein. For example, the actuator may take the form of a switch mounted on an exterior portion of the artificial rectum itself or adjacent thereto on the patient's body. For example, the actuator may take the form of a magnetic actuator magnetically coupled to a magnetic switch. Alternatively, the actuator may take the form of a sensor mounted on or adjacent to the artificial rectum for sensing the presence of fecal matter at the tissue ingrowth collar 18 or other appropriate location, or a pressure sensor for sensing the pressure at the tissue ingrowth collar 18 or other appropriate location. In either case, the sensor may transmit a signal to the patient to operate the artificial rectum, or may automatically operate the artificial rectum upon sensing the presence of fecal matter or sensing a pressure greater than a predetermined threshold pressure.

A one-way valve 52 extends laterally through a side wall of the inner body 30 and is coupled in fluid communication with an outlet conduit 53 extending between the one-way valve and tissue ingrowth flange 20 to permit the release of gas located within the tissue ingrowth collar 18 through the artificial rectum and out of the patient's body. In the currently preferred embodiment of the present invention, the one-way valve 52 is a spring loaded ball-check valve wherein the ball surface is directed laterally inwardly on the inner body to preclude fouling of the flowpath with solid or semi-solid fecal matter. In operation, as gas collects in the lower intestine, pressure will increase until the spring force holding the ball against its seat is overcome, unseating the ball, and permitting gas to flow. As the gas is discharged, pressure will drop and the spring force will act to re-seat the ball and stop flow. As may be recognized by those skilled in the pertinent art based on the teachings herein, any of numerous other types of valves that are currently or later become known may be equally used for the valve 52 in order to provide a unidirectional flow path for intestinal gas, such as, for example, an elastomeric check valve or other check valves actuated by pressure.

In the operation of the artificial rectum 10, the patient removes the air-tight removable cover 48 and actuates the remote control unit 15 in order to defecate fecal matter. The remote control unit 15 transmits a signal to the receiver 50 to actuate the inlet valve 40 and start the motor 44 to rotatably drive the macerator-type pump 42 and, in turn, move feces from the tissue ingrowth collar 18 through the tissue ingrowth flange 20 to thereby discharge the fecal matter from the body. The colon naturally releases a mucous into the tissue ingrowth collar 18 and, in turn, into the inner body 30 to lubricate the interior surfaces of the inner body and thereby facilitate the movement of fecal matter therethrough. Upon completing the defecation, the patient actuates the remote control unit 15 to shut the inlet valve 40 and stop the motor 44. Then, the patient re-installs the air-tight removable cover 48 over the second outlet 38.

Figure 3:
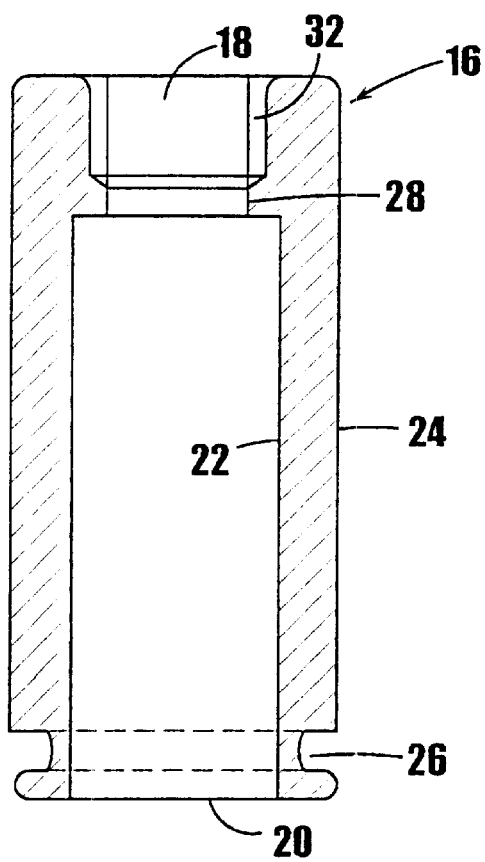
FIG. 3 is a cross-sectional view of the outer body of the artificial rectum of FIG. 2

Referring now to FIG. 3, the outer body 16 is substantially cylindrical in shape and defines the tissue ingrowth collar 18 on one end, the tissue ingrowth flange 20 on the other end, a first inner surface 22 and a first outer surface 24. The first outer surface 24 of the outer body 16 has an annular recess defining a mounting flange 26 at the tissue ingrowth flange 20 for surgical attachment to the patient's anal sphincter muscle or adjacent tissue, such as by surgical staples, as shown typically in FIG. 1.

Figure 4:
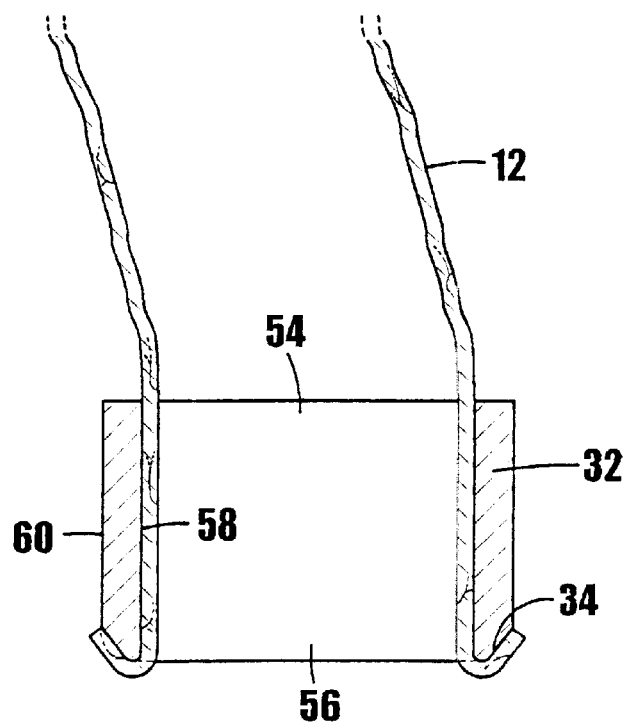
FIG. 4 is a cross-sectional view of the connector of the artificial rectum of FIG. 2.

Referring now to FIG. 4, the connector 32 is substantially cylindrical in shape and defines an inlet 54, an outlet 56, a connector inner surface 58, and connector outer surface 60. The connector 32 provides a means for mechanically affixing the distal end of the large intestine 12 to the tissue ingrowth collar 18 of the outer body 16 to thereby place the large intestine 12 in pressure-tight, fluid communication with the artificial rectum. The connector outlet 56 defines a bevel 34 formed so as to fully engage the beveled seating surface on the shoulder 28 of the outer body (FIG. 2). During installation of the artificial rectum, the distal end of the large intestine 12 is fed through the connector inlet 54 such that the distal end of the large intestine 12 protrudes out from the connector outlet 56. As shown typically in FIG. 4, the large intestine 12 is then drawn back over the beveled surface 34 to fixedly secure the large intestine to the connector upon slidably inserting the connector into the tissue ingrowth collar 18 of the outer body, as described above with reference to FIG. 2. As can be seen, the inner connector surface 58 is substantially cylindrical in shape and smooth in order to facilitate the flow of colon mucous naturally produced in the large intestine through the connector 32 and into the inner body 30. As shown in FIG. 2, the connector 32 is press fit into the tissue ingrowth collar 18 of the outer body 16 to seal the inlet to the artificial rectum and fixedly secure the distal end of the large intestine thereto. As may be recognized by those skilled in the pertinent art based on the teachings herein, this method of mechanical engagement between the connector, outer body, and large intestine is only exemplary, and any of numerous other ways that are currently, or later become known, may be equally employed to mechanically affix the distal end of the large intestine 12 to the tissue ingrowth collar 18 of the artificial rectum.

Figure 6:
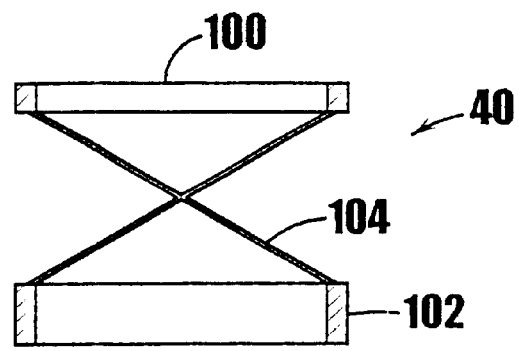
FIG. 6 is a cross-sectional view of a normally closed inlet valve of FIG. 2 in a closed position.

Referring now to FIG. 5A, the inner body 30 defines a second inlet 62, a second outlet 64, a second inner surface 66 and a second outer surface 68. As shown in FIG. 2, in the currently preferred embodiment of the present invention, the inner body 30 is substantially enclosed within the outer body 16. Referring now to FIG. 5B, the second inner surface 66 defines an upper annular recess 70 and a lower annular recess 72 for receiving an inlet ring 100 and an outlet ring 102, respectively, of the inlet valve 40 (FIG. 6). When assembled, an outer circumferential surface of the inlet ring 100 of the valve 40 is seated within the upper annular recess 70 of the inner body to fixedly mount the valve to the inner body 30. The outer circumferential surface of outlet ring 102 of the valve 40 likewise is seated within the lower annular recess 72 of the inner body 30, but with sufficient mechanical clearance to allow rotational movement of the outlet ring and some travel of the outlet ring in the axial direction upon opening and closing the valve. One advantage of the inner body assembly of the currently preferred embodiments of the present invention is that such a configuration permits the removal of the inner body 30 and its associated components while leaving the outer body 16 installed in the patient. Such removal may be required, for example, for subsequent post-surgical medical inspection of the colorectal cavity or replacement of moving components within the inner body 30.

Referring to FIG. 6, the inlet valve 40 is shown in the closed position, and includes the inlet ring 100, the outlet ring 102, and an elastomeric iris 104 appended to the inner circumference of the inner ring 100 and outlet ring 102 for controlling the flow of fecal matter therethrough. In the illustrated embodiment, the inlet valve 40 is mounted within the inner body 30 (FIG. 2) upstream of the pump 42. However, as may be recognized by those skilled in the pertinent art based on the teachings herein, the valve 40 may be located downstream of the pump if desired or otherwise required in a particular application. The inlet ring 100 and outlet ring 102 both define a recess through which fecal matter may flow when the inlet valve 40 is open. In the operation of the artificial rectum 10, the normally closed inlet valve 40 is opened by the receiver 50 which mechanically rotates the outlet ring 102 relative to the inlet ring 100, thereby allowing the elastomeric iris to retract from its normally twisted, closed position to an open position wherein the elastomeric iris is in a least distended, substantially cylindrical state. As may be recognized by those skilled in the pertinent art based on the teachings herein, the valve 40 may take the form of any of numerous different types of valves that are currently or later become known for performing the function of the valve as described herein. For example, the valve 40 could take the form of a gate valve or a pinch valve. Similarly, the valve may be actuated in any of numerous different ways that are currently known, or later become known, such as by RF, magnetic coupling, or electronic actuation.

Figure 7:
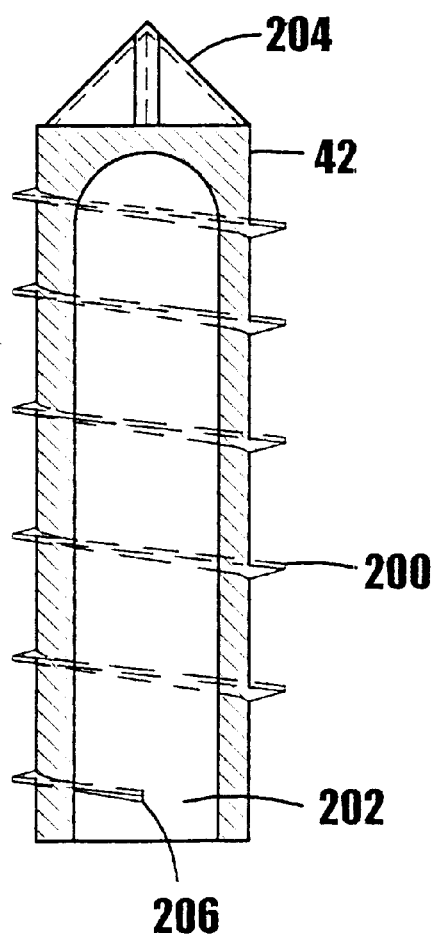
FIG. 7 is a cross-sectional view of the macerator-type pump of FIG. 2.

Referring to FIG. 7, the macerator-type pump 42 comprises a helical screw-type impeller 200 disposed around a hollow center shaft 202 and defining a leading edge 204 that protrudes conically from the top of the shaft 202 and a terminal edge 206. The impeller 200 is of a diameter so as to permit its rotation inside of the inner body and preclude the flow of fecal matter when not in operation. The impeller 200 is fixably mounted to the outer surface of the shaft such that when the shaft is rotatably driven by the motor 44 (FIG. 2), the helical impeller 200 is similarly driven. In operation, when the fecal matter flowing from the large intestine 12 comes in contact with the leading edge of the screw impeller 204, the rotation of the screw impeller creates a shearing force on the fecal matter, causing it to move down the thread of the screw impeller. As the fecal matter reaches the terminal edge of the impeller 206, the fecal matter is discharged as the screw impeller continues to turn, creating pressure high enough to force material through the tissue ingrowth flange 20 of the artificial rectum. One advantage of the macerator or screw-type pump is its ability to pump material of variable density without binding because of the relatively wide clearance between the flights of the screw impeller. As may be recognized by those skilled in the pertinent art based on the teachings herein, the pump may take any of numerous different configurations that are currently known, or later become known, for performing the function of the pump as described herein. For example, the pump 42 may take the form of a vacuum pump, or may take the form of a plurality of impellers axially disposed relative to each other.

While the subject invention has been described with respect to certain preferred embodiments, it will be appreciated by those skilled in the art that the principles and inventive concepts could be applied in any of numerous different applications. Further, those skilled in the art will readily appreciate that various changes and/or modifications can be made to the above-described and other embodiments of the present invention without departing from the spirit or scope of the invention as defined in the appended claims. For example, the components of the artificial rectum can be made of any of numerous different materials, or may take any of numerous different shapes and/or configurations that are currently or later become known. Similarly, the means for implanting the artificial rectum may take the form of surgical staples as described above, or may take the form of any of numerous other devices, structures or methods that are currently or later become known for purposes of surgically implanting such devices. In addition, the mechanism for connecting the artificial rectum to the large intestine may take any of numerous different configurations. For example, a tube, conduit or other connecting device may be connected between the inlet to the artificial rectum and the distal end of the large intestine. Accordingly, this detailed description of preferred embodiments is to be taken in an illustrative as opposed to a limiting sense.

What is claimed is:

1. An artificial rectum implantable in a patient for controlling defecation, comprising:
    a first body defining:
        an inlet connectable in fluid communication with a large intestine of the patient for receiving a flow of fecal matter therefrom; and
        an outlet coupled in fluid communication with the inlet for excreting fecal matter from the first inlet therethrough, and connectable to at least one of an anal sphincter of the patient and tissue adjacent to the anal sphincter of the patient;
    at least one flow control device coupled in fluid communication between the first inlet and the first outlet for controlling the passage of fecal matter from the first inlet through the first outlet; and
    an actuator coupled to the flow control device for controlling actuation of the flow control device and, in turn, controlling defecation by the patient.

2. An artificial rectum as recited in claim 1, wherein the first body further defines an annular recess for engaging the anal tissue of the patient.

3. An artificial rectum as recited in claim 1, further comprising a connector for connecting the colon in fluid communication to the inlet.

4. An artificial rectum as recited in claim 1, wherein the at least one flow control device is a pump.

5. An artificial rectum as recited in claim 1, wherein the at least one flow control device is a valve.

6. An artificial rectum as recited in claim 1, further comprising a second body releasably connected to the first body, wherein the second body defines a second inlet and a second outlet and the flow control device is coupled to the second body.

7. An artificial rectum as recited in claim 6, further comprising a cover for sealing the second outlet.

8. An artificial rectum as recited in claim 1, further comprising a gas-release valve.

9. An artificial rectum as recited in claim 1, wherein the actuator includes:
    a remote transmitter for sending a signal; and
    a receiver coupled to the flow control device for receiving the signal and actuating the flow control device in response thereto.

10. An artificial rectum implantable in a patient for controlling defecation, comprising:
    first means connectable in fluid communication with a large intestine of the patient for receiving a flow of fecal matter therefrom; second means connectable to at least one of an anal sphincter and tissue adjacent to the anal sphincter of the patient and coupled in fluid communication with the first means for excreting fecal matter therethrough;
    third means coupled in fluid communication between the first and second means for controlling the flow of fecal matter from the first means through the second means; and
    fourth means coupled to the third means for controlling actuation of the third means and, in turn, controlling the flow of fecal matter through the artificial rectum.

11. An artificial rectum as recited in claim 10, wherein the first means is defined by an inlet adapted to be fixably coupled to the large intestine of the patient and forming a pressure-tight seal with the large intestine.

12. An artificial rectum as recited in claim 10, wherein the second means is defined by an outlet adapted to be surgically attached to at least one of an anal sphincter and tissue adjacent to the anal sphincter.

13. An artificial rectum as recited in claim 10, wherein the third means is a pump.

14. An artificial rectum as recited in claim 10, wherein the third means is a valve.

15. An artificial rectum as recited in claim 10, wherein the fourth means is a receiver coupled to the third means for receiving a signal and actuating the third means in response thereto to induce a flow of fecal matter through the artificial rectum.

16. An artificial rectum as recited in claim 15, wherein the fourth means further includes a transmitter for transmitting the signal to the receiver.

17. An artificial rectum as recited in claim 10, further comprising fifth means for releasing gas through the artificial rectum.

18. An artificial rectum as recited in claim 17, wherein the fifth means is defined by a conduit adapted to be coupled in fluid communication between the large intestine and the exterior of the artificial rectum.

19. An artificial rectum as recited in claim 18, further comprising a valve coupled in fluid communication with the conduit for allowing the passage of gas through the conduit when the pressure on an inlet side of the valve exceeds a threshold value.

20. A method for providing an artificial rectum in a patient for controlling defecation, comprising the steps of:

providing an artificial rectum having an inlet, an outlet, and at least one flow control device coupled in fluid communication between the inlet and the outlet;

connecting the inlet of the artificial rectum in fluid communication with a large intestine of the patient;

connecting the outlet of the artificial rectum to at least one of an anus and a tissue adjacent to the anus of the patient;

receiving fecal matter from the large intestine through the inlet of the artificial rectum, and controlling the flow control device to selectively move the fecal matter between the inlet and the outlet, and, in turn, discharge the fecal matter through the outlet to thereby control defecation of the patient.

21. A method as recited in claim 20, wherein the step of connecting the inlet of the artificial rectum in fluid communication with a large intestine of the patient includes fixably securing the inlet of the artificial rectum to the large intestine.

22. A method as recited in claim 20, wherein the step of connecting the outlet of the artificial rectum to at least one of an anus and a tissue adjacent to the anus of the patient includes surgically attaching the outlet of the artificial rectum to at least one of an anus and a tissue adjacent to the anus of the patient.

23. A method as recited in claim 20, wherein the at least one flow control device includes a valve, and the step of controlling the flow control device to selectively move the fecal matter includes opening the valve and permitting the flow of fecal matter between the inlet and outlet, and closing the valve and preventing the flow of fecal matter between the inlet and outlet.

24. A method as recited in claim 20, wherein the at least one flow control device includes a pump, and the step of controlling the flow control device to selectively move the fecal matter includes actuating the pump to pump fecal matter between the inlet and the outlet.

25. A method as recited in claim 20, wherein the step of controlling the flow control device to selectively move the fecal matter between the inlet and the outlet includes remotely actuating the flow control device to move the fecal matter through the artificial rectum.

26. A method as recited in claim 20, wherein the step of receiving fecal matter from the large intestine includes receiving gases from the large intestine and venting the gases through the artificial rectum.

* * * * *